(12) United States Patent
Blake

(10) Patent No.: US 7,105,005 B2
(45) Date of Patent: Sep. 12, 2006

(54) ARTERIOTOMY SCISSORS FOR MINIMALLY INVASIVE SURGICAL PROCEDURES

(75) Inventor: Kenneth R. Blake, Brooklyn Park, MN (US)

(73) Assignee: Scanlan International, Inc., St. Paul, MN (US)

( * ) Notice: Subject to any disclaimer, the term of this patent is extended or adjusted under 35 U.S.C. 154(b) by 465 days.

(21) Appl. No.: 10/060,071

(22) Filed: Jan. 29, 2002

(65) Prior Publication Data
US 2002/0123763 A1 Sep. 5, 2002

Related U.S. Application Data

(60) Provisional application No. 60/264,885, filed on Jan. 29, 2001.

(51) Int. Cl.
*A61B 17/32* (2006.01)

(52) U.S. Cl. .................................................. 606/174

(58) Field of Classification Search ................ 606/167, 606/170, 174, 205–209
See application file for complete search history.

(56) References Cited

U.S. PATENT DOCUMENTS

| | | | |
|---|---|---|---|
| 4,258,716 A * | 3/1981 | Sutherland | 606/174 |
| 5,009,661 A * | 4/1991 | Michelson | 606/205 |
| 5,172,479 A | 12/1992 | Keeton | |
| 5,193,277 A | 3/1993 | Zmijewski | |
| 5,275,607 A | 1/1994 | Lo et al. | |
| 5,370,658 A * | 12/1994 | Scheller et al. | 606/205 |
| 5,496,347 A | 3/1996 | Hashiguchi et al. | |
| 5,584,845 A | 12/1996 | Hart | |
| 5,762,458 A | 6/1998 | Wang et al. | |
| 5,792,165 A * | 8/1998 | Klieman et al. | 606/174 |
| 5,807,377 A | 9/1998 | Madhani et al. | |
| 5,810,877 A * | 9/1998 | Roth et al. | 606/205 |
| 5,827,323 A * | 10/1998 | Klieman et al. | 606/205 |
| 5,855,583 A | 1/1999 | Wang et al. | |
| 5,944,729 A | 8/1999 | Blake | |
| 6,007,550 A | 12/1999 | Wang et al. | |
| 6,102,850 A | 8/2000 | Wang et al. | |
| 6,132,441 A | 10/2000 | Grace | |
| 6,309,397 B1 | 10/2001 | Julian et al. | |
| 6,312,435 B1 | 11/2001 | Wallace et al. | |
| 6,339,884 B1 | 1/2002 | Liu | |
| 6,398,726 B1 | 6/2002 | Ramans et al. | |
| 6,436,107 B1 | 8/2002 | Wang et al. | |
| 6,517,552 B1 * | 2/2003 | Nord et al. | 606/207 |

OTHER PUBLICATIONS

Scanlan International "Spring Style Micro Scissors, Angled Blades Collection" brochure, 8 pages, 2002.
Super Cut & Ultra Sharp scissors collection brochure, 2000 Scanlan International, Inc.

* cited by examiner

*Primary Examiner*—Eduardo C. Robert
*Assistant Examiner*—Jessica R. Baxter
(74) *Attorney, Agent, or Firm*—Faegre & Benson LLP

(57) ABSTRACT

An arteriotomy scissors for a surgical system including a sleeve, a fixed blade fixedly mounted to a distal end of the sleeve, a movable blade pivotally mounted to the fixed blade and the distal end of the sleeve, and an actuation rod extending through the sleeve. The movable blade is mounted to a distal end of the actuation rod. The actuation rod is driven in a reciprocal manner within the sleeve to drive the movable blade between a fully open cutting position and a fully closed cutting position with respect to the fixed blade.

12 Claims, 4 Drawing Sheets

ARTERIOTOMY SCISSORS FOR MINIMALLY INVASIVE SURGICAL PROCEDURES

This application claims the benefit of U.S. Provisional Application Ser. No. 60/264,885 filed Jan. 29, 2001.

FIELD OF THE INVENTION

The present invention relates to surgical instruments. More specifically, the present invention is an arteriotomy scissors for use in connection with minimally invasive surgical procedures.

BACKGROUND OF THE INVENTION

The use of minimally invasive procedures for cardiac and other surgery continues to develop. A method and apparatus of this type is disclosed, for example, in the Wang et al. U.S. Pat. No. 6,007,550. There remains, however, a continuing need for improved procedures and instruments for minimally invasive surgery.

SUMMARY OF THE INVENTION

This invention is an arteriotomy scissors for minimally invasive surgical procedures. One embodiment of the invention includes a sleeve, a fixed blade fixedly mounted to the distal end of the sleeve, a movable blade pivotally mounted with respect to the fixed blade at the distal end of the sleeve, and an actuation rod extending through the sleeve. The actuation rod is mounted to the movable blade and is driven in a reciprocal manner within the sleeve for causing the movable blades to move with respect to the fixed blade. The fixed and movable blades form a cutting gap that opens in a direction generally perpendicular to the longitudinal axis of the sleeve.

Another embodiment the invention includes a sleeve, a pair of cutting blades mounted to the distal end of the sleeve, and an actuation member for causing the blades to move between open and closed cutting positions. The cutting blades form a cutting gap that opens in a direction generally perpendicular to the longitudinal axis of the sleeve.

BRIEF DESCRIPTION OF THE DRAWINGS

FIG. 3A is a sectional view of the scissors taken along line A—A in FIG. 3.

FIG. 3B is a sectional view of the scissors taken along line B—B in FIG. 3.

DETAILED DESCRIPTION OF THE INVENTION

Figure 5:
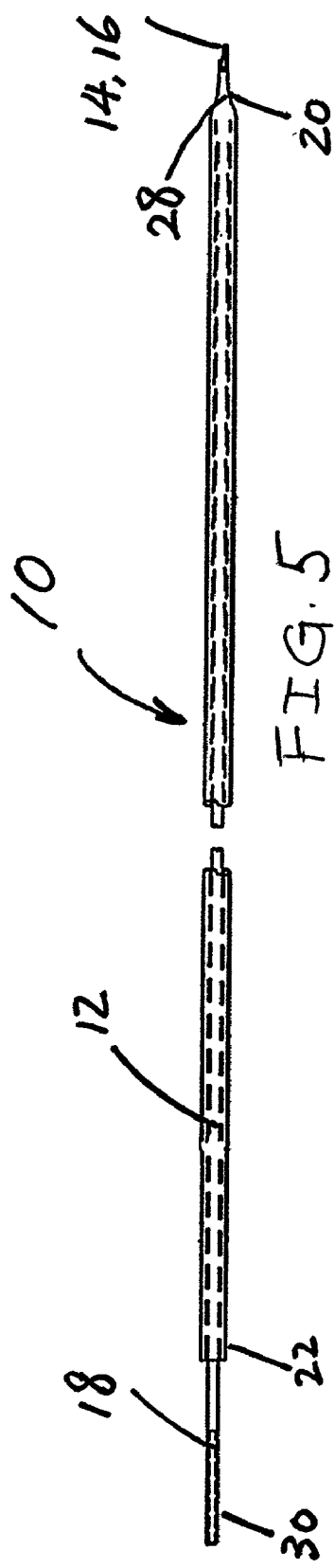
FIG. 5 is a top view of the arteriotomy scissors shown in FIG. 1.

A preferred embodiment of an arteriotomy scissors 10 in accordance with the present invention is described generally with reference to FIGS. 1–5. As shown, the arteriotomy scissors 10 comprises a sleeve 12, a fixed blade 14, a movable blade 16, and an actuation rod 18. The sleeve 12 includes a longitudinal axis 34, a distal end 20, and a proximal end 22. The actuation member or rod 18, including a distal end and a proximal end 30, extends through the sleeve 12 along the longitudinal axis 34. The fixed blade 14 is fixedly mounted to the distal end 20 of the sleeve 10. The movable blade 16 pivots about a pivotal axis 26 with respect to the fixed blade 14 in a scissors type cutting action. The movable blade 16 pivotally moves in a plane perpendicular to the pivotal axis 26. The movable blade 16 is pivotally mounted with respect to the fixed blade 14 at the distal end 20 of the sleeve 12 by a pivot pin or a pivot screw. The fixed blade 14 and the movable blade 16 are oriented at an angle with respect to the sleeve 12.

Figure 1:
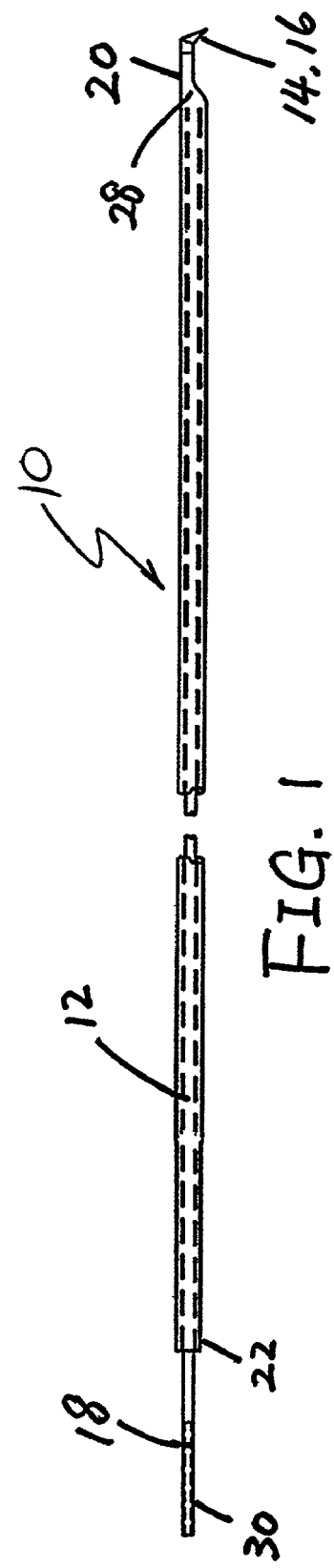
FIG. 1 is a side view of an arteriotomy scissors in accordance with the present invention.
Figure 2:
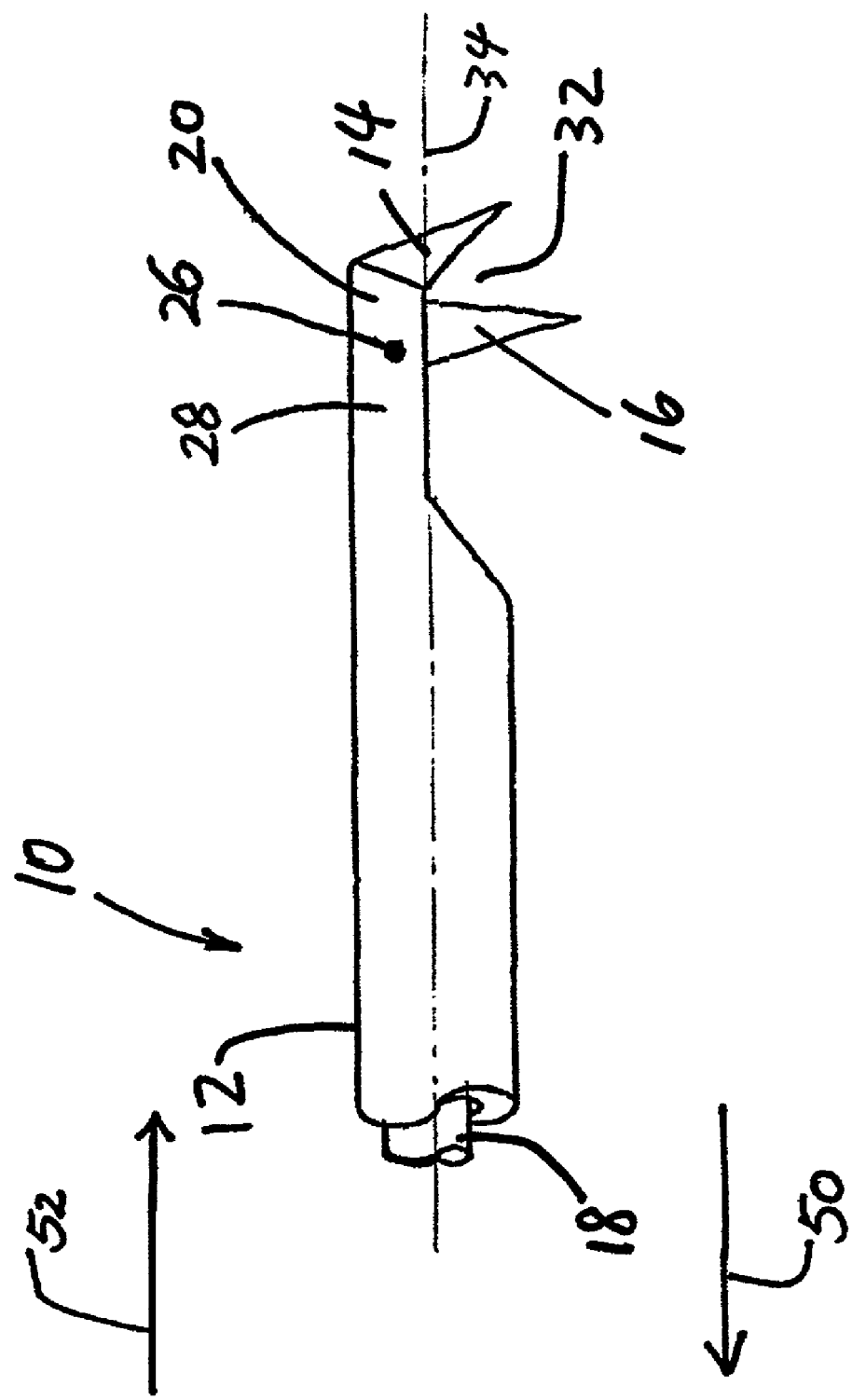
FIG. 2 is a detailed side view of the arteriotomy scissors shown in FIG. 1, showing a movable blade in an open cutting position with respect to a fixed blade.

The distal end of the actuation rod 18 is mounted to the movable blade 16 inside the sleeve 12 at the distal end 20 of the sleeve 12. The actuation rod 18 is driven in a reciprocal manner within the sleeve 12 to drive the movable blade 16 between a fully open cutting position and a fully closed cutting position with respect to the fixed blade 14. In particular, when the actuation rod 18 is pulled at the proximal end 30 in a direction 50 along the longitudinal axis 34 of the sleeve 12, the movable blade 16 is driven pivotally toward the fixed blade 14 to form a closed cutting position. Conversely, when the actuation rod 18 is pushed at the proximal end 30 in a direction 52 along the longitudinal axis 34, the movable blade 16 is driven pivotally away from the fixed blade 14 to form an open cutting position. FIG. 1 shows that the movable blade 16 in the closed cutting position with respect to the fixed blade 14. FIG. 2 shows the movable blade 16 in the open cutting position with respect to the fixed blade 14. Mechanical linkages other than rod 18 can be used to actuate blade 16. In yet other embodiments of the invention, both blades 14 and 16 can be actuated.

Figure 3:
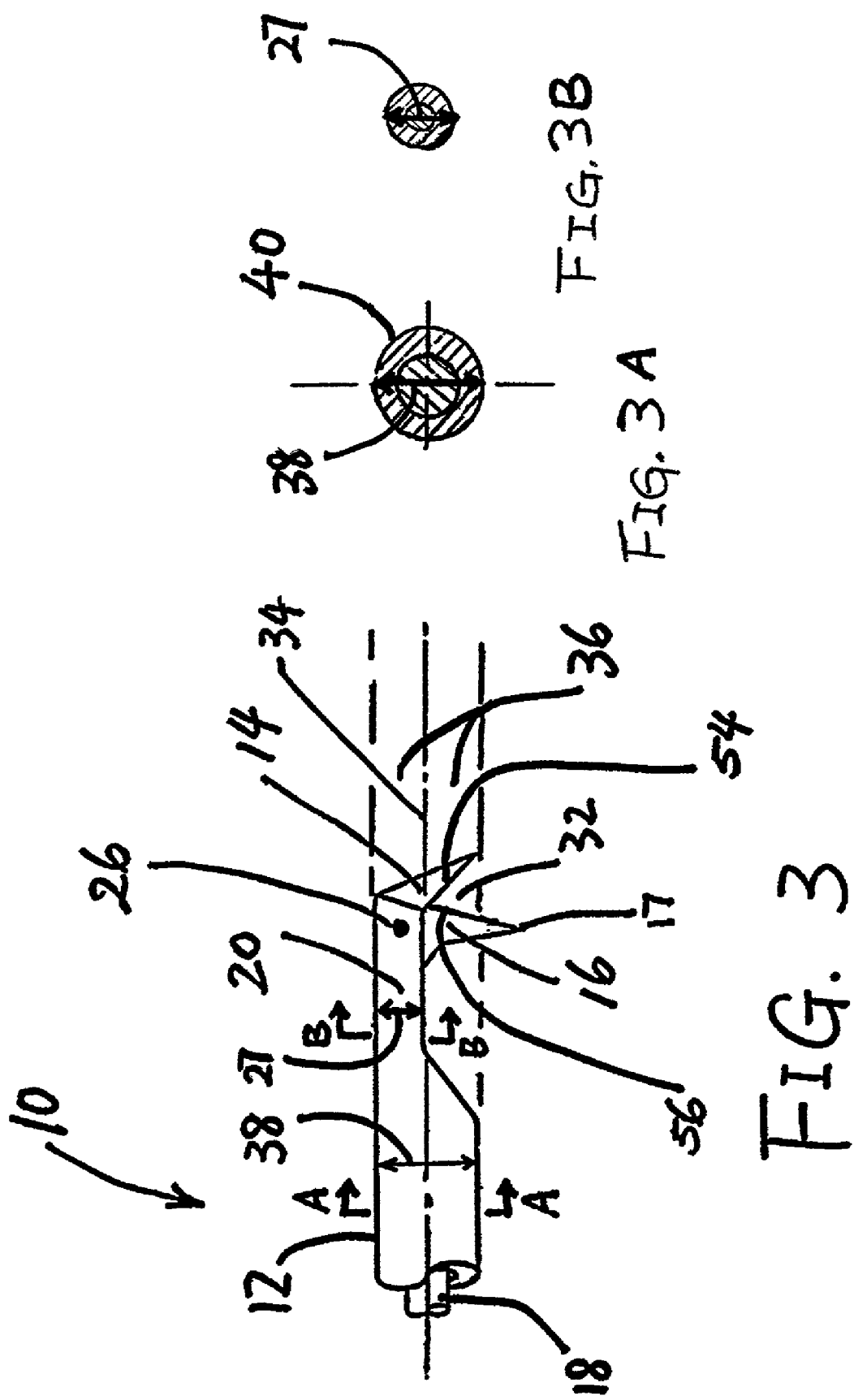
FIG. 3 is a detailed side view of the arteriotomy scissors, showing the movable blade in an open cutting position with respect to the fixed blade and an imaginary projection space along the longitudinal axis defined by an outer perimeter of a cross section of the sleeve.

As shown in FIG. 3, the moving blade 16 is in the open cutting position with respect to the fixed blade 14. In this position, a cutting edge 54 of the fixed blade 14 and a cutting edge 56 of the movable blade 16 define a cutting gap 32 therebetween. The cutting gap 32 is oriented in a substantially perpendicular direction with respect to the longitudinal axis 34 of the sleeve 12. The dimension (e.g., diameter 38 or outer perimeter 40) of the cross section of the sleeve 12 is reduced at the distal end 20 of the sleeve 12. The cross-sectional view 3A shows the cross section of the sleeve 12 with the diameter 38, and the cross-sectional view 3B shows the reduced cross section of the sleeve 12 with a reduced diameter 27 at the distal end 20. The outer perimeter 40 of the cross section shown in FIG. 3A defines a projection space 36 along the longitudinal axis 34 of the sleeve 12. The fixed blade 14 is completely located within the projection space 36 in the embodiment shown. When the movable blade 16 is in the closed cutting position with respect to the fixed blade 14, the complete portion of the movable blade 16 is also located within the projection space 36 in this embodiment. As shown in FIG. 3, when the movable blade 16 is in the fully open cutting position with respect to the fixed blade 14, a substantial portion of the movable blade 16 is preferably located within the projection space 36. In this fully open cutting position, the tip portion 17 of the movable blade 16 is located outside the projection space 36, and a substantial portion of the cutting gap 32 between the cutting edge 54 of the fixed blade 14 and the cutting edge 56 of the movable blade 16 is located within the projection space 36. It is also noted that the thickness of the movable blade and the fixed blade is less than the reduced diameter section 28 of the sleeve.

One preferred embodiment of the arteriotomy scissors 10 of the present invention has an overall length of about 352.0 mm. In this embodiment the cross section of the sleeve 12 throughout all but section 28 has a diameter 38 of about 3.4 mm. The cross section of the sleeve 12 at the distal end 20 preferably has a reduced diameter 27 of about 1.6 mm. The length of the reduced diameter section 28 is about 6.6 mm in this embodiment.

Figure 4:
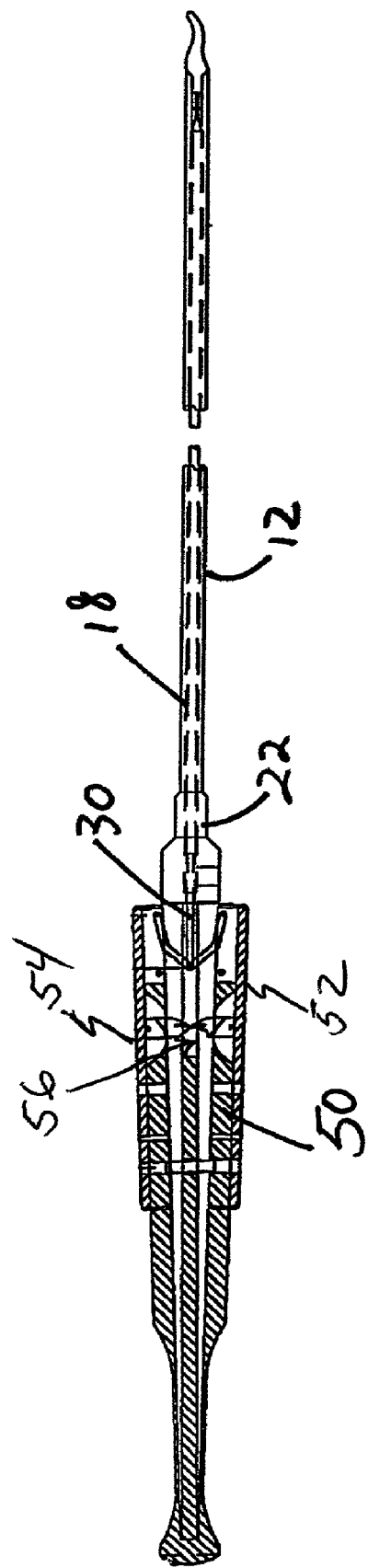
FIG. 4 is a cross-sectional side view of the arteriotomy scissors, with a mechanical actuation structure mounted to its proximal end.

It is to be understood that the proximal end 22 of the sleeve 12 and the proximal end 30 of the actuation rod 18 are configured to be mounted to a surgical system, e.g. an arm of a robot such as that shown in U.S. Pat. No. 6,007,550 (not shown). In addition, as shown in FIG. 4, the proximal end 22 of the sleeve 12 and the proximal end 30 of the actuation rod 18 may be configured to be mounted to a mechanical actuation system 50.

System 50 includes handle/lever arms 52 and 54 and a linkage 56 that couples the handle/lever arms to rod 18. When grasped by a surgeon and squeezed, handle/lever arms 52 and 54 are moved together from a released position at which the linkage 56 causes the blades 14 and 16 to be in the open cutting position, to a locked position at which the blades 14 and 16 are in the closed cutting position. If the surgeon releases their grip from the handle/lever arms 52 and 54 when the handle/lever arms are in the locked position, or squeezes them no further together, the handle/lever arms will remain in the locked position with the blades 14 and 16 in the closed cutting position. When the handle/lever arms 52 and 54 are squeezed together further from the locked position, they are moved to an unlock position from which the spring bias force on the handle/lever arms will return the arms to the release position. The linkage 56 allows the handle/lever arms 52 and 54 to move directly between the release and unlock positions if the arms are squeezed through the locked position, thereby allowing a surgeon to reciprocate blades 14 and 16 between open and closed cutting positions through a continuous squeezing and releasing motion.

In a preferred method of use, the arteriotomy scissors 10 provides for a right angle approach through a minimal access port (e.g., 3.8 mm in diameter) to a patient, thereby enabling a surgeon to extend an incision in the patient's coronary artery to perform an anastomosis with a vessel (not shown). Initially, a scalpel attachment can be used to make a small incision in the coronary artery of the patient. The arteriotomy scissors 10 is opened to form a cutting gap between the cutting edge 54 of the fixed blade 14 and the cutting edge 56 of the movable blade 16. The fixed blade 14 of the arteriotomy scissors 10 is inserted into the incision in the coronary artery. The arteriotomy scissors 10 is operated to extend the arteriotomy distally. The arteriotomy scissors 10 is then removed from the artery. Subsequently, the arteriotomy scissors 10 is rotated. The fixed blade 14 is then reinserted into the incision in the coronary artery. Finally, the arteriotomy scissors 10 is operated to extend the arteriotomy proximally. A precision approach from the access port can thereby be achieved by the arteriotomy scissors.

Although the present invention has been described with reference to preferred embodiment, those skilled in the art will recognize that changes can be made in form and detail without departing from the spirit and scope of the invention. In particular, although the disclosed embodiments of the arteriotomy scissors is described in connection with a procedure for extending an incision in a patient's coronary artery to perform an anastomosis with a vessel, it is contemplated that the invention is suitable for other surgical operations.

What is claimed is:

1. An arteriotomy scissors comprising:
   a sleeve having a longitudinal axis, a distal end, and a proximal end, the distal end having a first region with a first cross section dimension and a second region with a second, reduced cross section dimension that is fixedly positioned with respect to the first region;
   a fixed blade having a cutting edge fixedly mounted to the second region at the distal end of the sleeve;
   a movable blade having a cutting edge pivotally mounted with respect to the fixed blade to the second region at the distal end of the sleeve;
   the cutting edge of one of the fixed and movable blades extending at an angle less than ninety degrees with respect to the sleeve longitudinal axis, and the cutting edge of the other of the fixed and moveable blades extending at an angle greater than ninety degrees with respect to the sleeve longitudinal axis, to form a cutting gap that opens in a direction generally perpendicular to the longitudinal axis of the sleeve and, wherein the cutting gap formed by the fixed blade and the movable blade is substantially located within a projection space along the longitudinal axis defined by an outer perimeter of the cross section of the first region of the sleeve distal end and the movable blade is substantially located within the projection space when the movable blade is in an open cutting position with respect to the fixed blade; and
   an actuation rod having a distal end and a proximal end, the actuation rod extending through the sleeve, and the distal end of the actuation rod mounted to the movable blade.

2. The arteriotomy scissors of claim 1 wherein the movable blade pivots about a pivotal axis with respect to the fixed blade in a scissors type cutting action and moves in a plane perpendicular to the pivotal axis.

3. The arteriotomy scissors of claim 1 wherein the actuation rod is driven in a reciprocal manner within the sleeve to drive the movable blade between a fully open cutting position and a fully closed cutting position with respect to the fixed blade.

4. The arteriotomy scissors of claim 1 wherein the fixed blade and the movable blade are oriented at an angle with respect to the sleeve.

5. The arteriotomy scissors of claim 1 wherein the fixed blade is fully located within a projection space along the longitudinal axis defined by an outer perimeter of the cross section of the first region of the sleeve distal end.

6. The arteriotomy scissors of claim 1 wherein the fixed blade has a thickness less than a diameter of a cross section of the sleeve.

7. The arteriotomy scissors of claim 1 wherein the movable blade has a thickness less than a diameter of a cross section of the sleeve.

8. The arteriotomy scissors of claim 1 wherein the proximal end of the sleeve and the proximal end of the actuation rod are configured to be mounted to a surgical system.

9. An arteriotomy scissors comprising:
   a sleeve having a longitudinal axis, a distal end, a proximal end, the distal end having a first region with a first cross section dimension and a second region with a second, reduced cross section dimension that is fixedly positioned with respect to the first region;

a pair of cutting blades having cutting edges mounted to the second region on the distal end of the sleeve and located substantially within a space defined by a projection of the first region of the sleeve, wherein one of the cutting edges forms an angle less than ninety degrees with respect to the sleeve longitudinal axis and the other cutting edge forms an angle greater than ninety degrees with respect to the sleeve longitudinal axis;

the cutting blades forming a cutting gap that opens in a direction generally perpendicular to the longitudinal axis of the sleeve and is located substantially within a space defined by a projection of the first region of the sleeve; and an actuation member for causing the blades to move between open and closed cutting positions.

10. The arteriotomy scissors of claim 9 wherein the blades are oriented at an angle with respect to the sleeve.

11. The arteriotomy scissors of claim 9 wherein at least one of the blades has a thickness less than a diameter of a cross section of the first region of the sleeve.

12. The arteriotomy scissors of claim 9 wherein the proximal end of the sleeve and a proximal end of the actuation member are configured to be mounted to a surgical system.

* * * * *